United States Patent [19]

Hochmair et al.

[11] 4,357,497
[45] Nov. 2, 1982

[54] SYSTEM FOR ENHANCING AUDITORY STIMULATION AND THE LIKE

[76] Inventors: Ingeborg J. Hochmair; Erwin S. Hochmair, both of Jaunerstr 27, A-1130, Vienna, Austria

[21] Appl. No.: 267,405

[22] Filed: May 26, 1981

Related U.S. Application Data

[63] Continuation-in-part of Ser. No. 77,791, Sep. 24, 1979, Pat. No. 4,284,856.

[51] Int. Cl.³ .............................................. H04R 25/02
[52] U.S. Cl. ........................... 179/107 E; 179/107 BC
[58] Field of Search ............ 179/107 BC, 107 E, 1 A, 179/1 D, 1 AA, 1 SA

[56] References Cited

U.S. PATENT DOCUMENTS 4,284,856  8/1981  Hochmair et al. .............. 179/107 E Primary Examiner—Thomas A. Robinson
Attorney, Agent, or Firm—Orrin M. Haugen; Thomas J. Nikolai

[57] ABSTRACT

A plurality of the carrier signals are modulated by signals in the audio frequency bands. The carrier signals are transmitted to a receiver having one or more independent channels for receiving and demodulating the transmitted signals. The detected signals are applied to electrodes on a prosthetic device implanted in the cochlea with the electrodes selectively positioned in the cochlea to stimulate regions having a desired frequency response.

17 Claims, 18 Drawing Figures

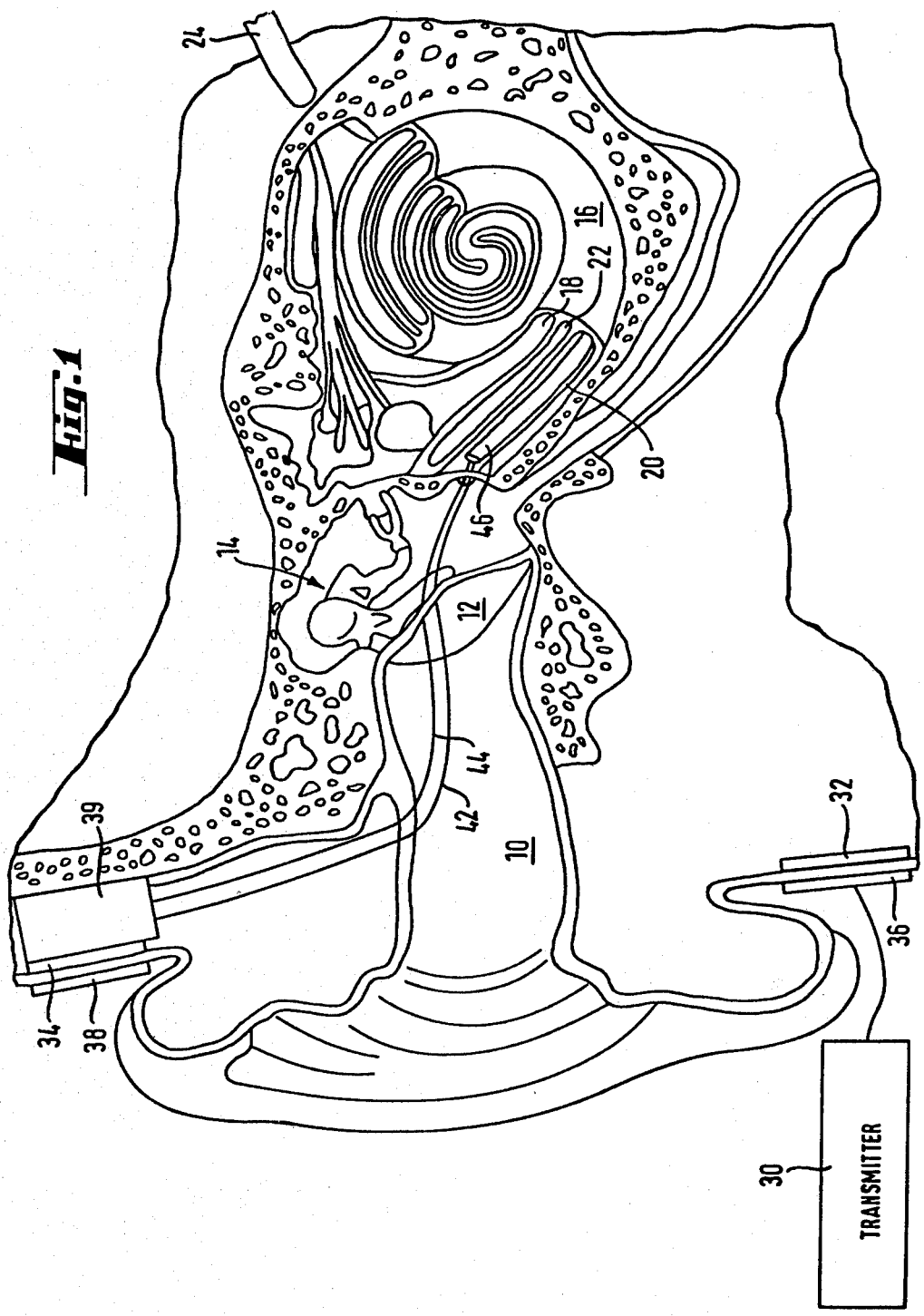

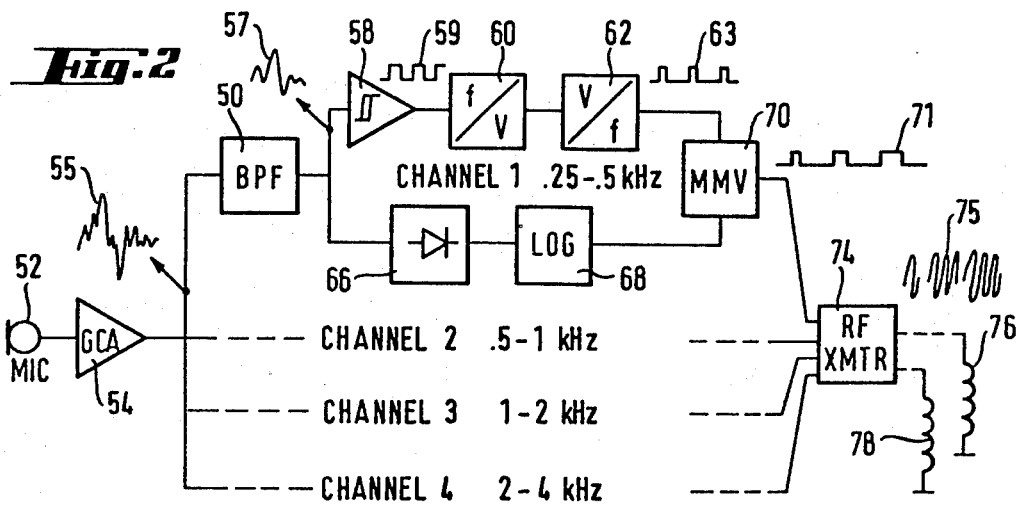
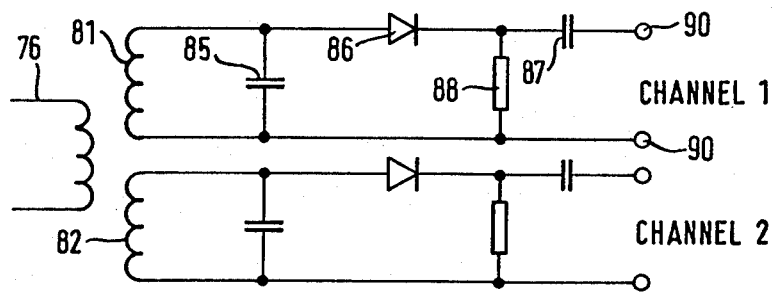
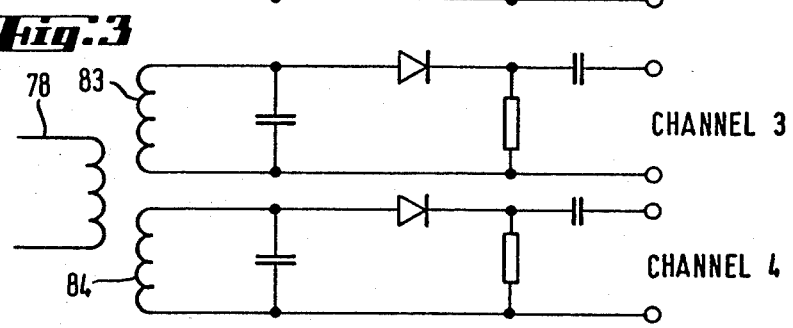
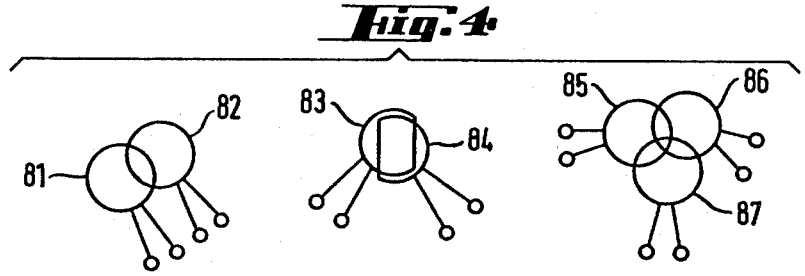

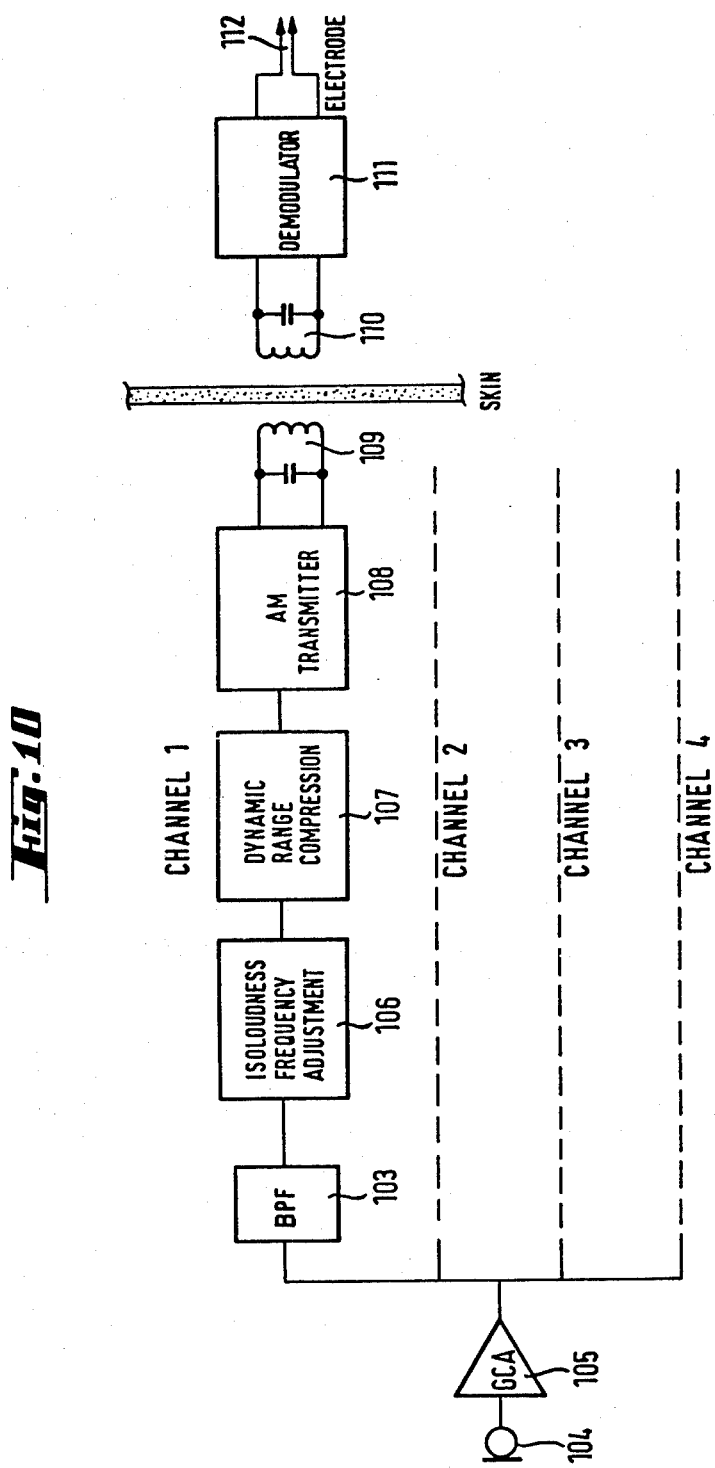

SYSTEM FOR ENHANCING AUDITORY STIMULATION AND THE LIKE

CROSS-REFERENCE TO RELATED APPLICATION

The present application is a continuation-in-part application of a U.S. application by Ingeborg J. Hochmair and Erwin S. Hochmair. The parent case is U.S. Ser. No. 77,791 filed Sept. 24, 1979 and entitled MULTI-FREQUENCY SYSTEM AND METHOD FOR ENHANCING AUDITORY STIMULATION AND THE LIKE now U.S. Pat. No. 4,284,856.

BACKGROUND OF THE INVENTION

This invention relates generally to apparatus for neural and muscle stimulation such as for facilitating hearing in the deaf, and more particularly the invention relates to a method and means for stimulating by means of electrical pulses.

The use of subcutaneously implanted hearing devices is known. U.S. Pat. No. 3,209,081 discloses a device which is implanted in the mastoid bone. The receiver makes direct contact with the bone through which sound waves may be conducted to the inner ear.

More recently, implanted prosthetic devices for stimulating the auditory nerve by means of electrical pulses have been disclosed. U.S. Pat. No. 3,449,768 discloses the use of coded pulse trains to create an electrical gradient field to facilitate visual or audio stimulations, U.S. Pat. No. 3,752,939 discloses the use of an electrode including a pair of elongated conductors for implanting in the cochlea.

Schindler et al., "Multielectrode Intracochlear Implants" Arch Otolaryngol, Vol. 103, December 1977, discloses the use of spatial excitation of the cochlear nerve in cats. Clark and Hallworth, "A Multiple-Electrode Array for Cochlear Implant," J. Laryngol, Otol, 90/7, 1976 discloses a ribbon array including a plurality of elongated flat electrodes which are positioned along the length of the cochlea for stimulating the auditory nerve. Similarly, bundles of thin wires have been employed by the Stanford Auditory prosthesis group by direct placement into the auditory nerve.

European patent application No. 78300567.1 by Foster et al. and German Pat. No. 2,823,798 by Hochmair et al. both describe multi-channel implantable hearing aids for the deaf containg active circuits.

OBJECTS

An object of the present invention is an improved system for neural and muscle stimulation.

Another object of the invention is an improved method of enhancing auditory stimulation by means of multiple electrode stimulation.

Still another object of the invention is in the provision of particular electrode means for selectively applying electrical stimulation to the auditory nerve.

Yet another object of the invention is to provide electrode means which can be readily inserted into the cochlea.

Another object of the invention is a method of making a multielectrode prosthetic device for cochlea excitation.

A feature of the invention also resides in the transmission of signals corresponding to bands of audio frequencies.

Another feature of the invention resides in the use of a receiver having independent channels for processing signals corresponding to audio frequency bands.

Still another feature of the invention comprises the use of electrode means for applying signals corresponding to audio frequency bands to selected regions in the cochlea.

SUMMARY OF THE INVENTION

Briefly, in accordance with the invention the system for enhancing audio stimulation, typically includes a single channel or multi-channel transmission means for transmitting one or a plurality of signals, each of which is modulated by a signal representing a band of frequencies in the audio range. A single channel or multi-channel receiver means for subcutaneous placement is provided for receiving the transmitted signals with each channel of the receiver responsive to one of the transmitted signals representing a band of frequencies. In a preferred embodiment, each channel of the receiver is independent and includes a tuned receiving coil for receiving a transmitted signal and detector means for detecting the transmitted modulation signal.

A multi-electrode prosthetic device is provided for cochlea implantation with means connecting a signal from each of the receiver channels to at least one electrode pair of the prosthetic device whereby the prosthetic device provides electrical stimulation to the auditory nerve. Placement of the electrodes in the device is chosen whereby the implanted device will stimulate the cochlea in accordance with the frequency response thereof.

The multi-electrode prosthetic device preferably comprises a molded biocompatible body with two or more wires within the body. Each wire is terminated in a contact body, such as a conductive ball, with the ball positioned at the surface of the body. Advantageously, each wire is wrinkled prior to the molding of the body to provide stress relief and facilitate flexing of the prosthetic device for insertion into the cochlea. The balls at the end of the wires are selectively positioned whereby the inserted prosthetic device stimulates the cochlea in accordance with the frequency response of the cochlea.

In a preferred embodiment, each channel of the transmission means includes a band pass filter for selecting and passing a band of audio frequency signals, a pulse generator, means responsive to the frequency of signals passed by the band pass filter for controlling the frequency of the pulse generator, and means responsive to the amplitude of signals passed by the band pass filter for controlling pulse width in the pulse generator. The output signal from the pulse generator is applied to modulate a carrier frequency in a transmitter.

The signal from the transmission means is transmitted to the receiver by means of a coil connected to the transmitter output. In accordance with one arrangement, a multi-channel receiver includes a plurality of coil corresponding in number to the number of channels of the receiver, the transmitter coil being the receiver coils are magnetically coupled in a substantially non-interfering manner. The receiver coils may be provided in spaced apart groups with the coils in each group overlapping to minimize magnetic coupling effects of the receiver coils.

In an alternative arrangement, instead of employing pulse-type circuitry in the transmitter, analogue type signal processing circuitry is employed. Specifically, each channel in the multi-channel speech processing transmitter includes a band pass filter for providing channelization of the picked-up and amplified sound waves. But now, instead of creating pulse type waveforms and utilizing frequency-to voltage and voltage-to frequency pulse type converter circuits as in the digital implementation, an isoloudness frequency adjustment network and a dynamic range compression network are used to process the waveforms before they are applied, via a coupling network, to the prosthetic device implanted in the cochlea. Typically, the coupling network may be an amplitude modulated transmitter which drives a tuned transmitting coil. The amplitude modulated carrier is thereby transmitted through body tissue to the implanted receiver module which functions to demodulate the received waveform with the envelope signal being applied to the prosthetic device implanted in the cochlea. Alternatively, the coupling network may be a percutaneous plug whereby the signals emanating from the signal processing channel(s) may be conductively coupled to the implanted prosthetic device.

The invention and objects and features thereof will be more readily apparent from the following detailed description and appended claims when taken with the drawings, in which:

DESCRIPTION OF THE DRAWINGS

FIG. 1 is a section view of a human ear illustrating the application of the present invention.

FIG. 2 is an electrical schematic of a transmitter for use in the multi-frequency system for enhancing audio stimulation in accordance with one embodiment of the present invention.

FIG. 3 is an electrical schematic of one embodiment of a multiple channel receiver for use in a multi-frequency system for enhancing audio stimulation in accordance with the invention.

FIG. 4 is a plan view illustrating the placement of receiver coils in accordance with one embodiment of the invention.

FIG. 10 is a block diagram of a multi-channel, portable sound processor/transmitter utilizing analogue techniques.

DESCRIPTION OF THE PREFERRED EMBODIMENT

Figure 5:
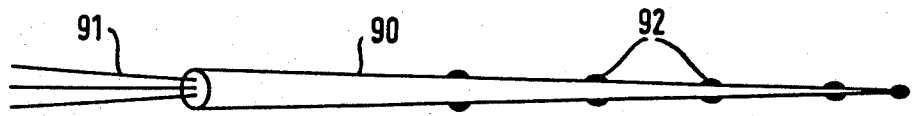
FIG. 5 is a perspective view of one embodiment of a multi-electrode prosthetic device in accordance with the invention.

Referring now to the drawings, FIG. 1 is a section view of a human ear illustrating the application of a multi-frequency audio stimulation system in accordance with the present invention. Normally, sounds are transmitted through the outer ear 10 to the eardrum 12 which moves the bones of the middle ear, shown generally at 14, and excites the cochles, shown generally at 16. The cochlea is a long narrow duct, wound spirally about its axis for approximately two and one-half turns. The cochlea includes an upper channel 18, the "scala vestibuli," and a lower channel 20, the "scala tympani," with the cochlear duct 22 therebetween. The fluid-filled scala vestibuli and scala tympani transmit waves in response to received sounds and in cooperation with the cochlear duct 22, function as a transducer to generate electric pulses which are transmitted to the cochlear nerve 24 and thence to the brain.

In people with total sensorineural hearing loss the cochlea does not respond to sound waves to generate electrical signals which can be transmitted to the cochlear nerve. The multi-frequency stimulation system in accordance with the present invention effects direct electrical stimulation of the cochlea. The system includes a multi-frequency transmitter 30 which may be worn on the body. The transmitter is coupled to an implanted receiver. The coupling is preferably accomplished by means of coils 36 and 38 which are connected to the multi-channel transmitter 30 and coils 32 and 34 associated with the receiver. As will be described hereinbelow in detail, the transmitter 30 transmits a plurality of signals which are modulated in accordance with the signal content of a plurality of audio frequency bands. The transmitted signals are received and detected in the receiver with the detected signal connected through wires 42 and 44 to a prosthetic device 46 which is implanted in the cochlea. As will be described further hereinbelow, the prosthetic device includes a plurality of electrodes which are positioned on the surface of the device to provide selective stimulation of the cochlea in accordance with the frequency response thereof.

In one embodiment, the multi-frequency system includes four channels corresponding to four frequency bands in the audio frequency range. FIG. 2 is an electrical schematic of an embodiment of the transmitter which uses pulse-type circuitry and includes four channels corresponding to 0.25–0.5 Khz, 0.5–1.0 Khz, 1.0–2.0 Khz, and 2.0–4.0 Khz. The circuitry for each channel is illustrated in block diagram form in channel 1 and includes a band pass filter 50 tuned for the desired frequency band (e.g. 0.25–0.5 Khz for channel 1). Filter 50 receives an audio signal picked up by a microphone 52 and passed through a gain controlled amplifier 54. The signal from amplifier 54 has a wide frequency range as illustrated at 55, and after passing through the bandpass filter 50, a signal of limited frequency range is provided as shown at 57. Delay circuitry can be included in the lower frequency channels to compensate for the delay normally introduced in transmitting acoustic waves through the length of the cochlea for stimulating the lower frequency stimulation sites near the apex of the cochlea.

The signal 57 is then applied through a limiter 58 which produces a clipped output signal 59 showing the same zero-crossings as wave 57. The clipped wave 59 is applied to a frequency-to-voltage converter 60 which produces a time varying dc voltage that is proportional to the frequency of signal 59. The frequency-to-voltage converter comprises suitable circuitry, such as a monostable multivibrator which is triggered by signal 59 to generate a plurality of pulses of equal pulse width and having a repetition rate corresponding to the frequency of the signal 59. The monostable multivibrator output is passed through a low pass filter to generate a time varying dc voltage which is proportional to the pulse rate.

The time varying voltage output from converter 60 is then applied to a voltage-to-frequency converter 62 such as a voltage controlled oscillator which generates an output signal 63 comprising a train of pulses having a fixed pulse width and a frequency corresponding to the voltage applied to the voltage controlled oscillator. However, the frequency range of the pulse train 63 may vary in a limited range such as 40–400 Hz while the band-pass filter passes a smaller or larger frequency range. As will be described further hereinbelow, the auditory nerve can detect signal pitch wherein excitation is limited to electrical pulses at a frequency limited to 400 Hz applied to particular stimulation sites in the cochlea. Thus, the passband is transformed into a lower frequency range corresponding to the range of electrical stimulation frequency where pitch discrimination can be achieved. This range is in most cases limited to e.g. 40–400 Hz, although it might also be considerably larger in certain cases.

The signal from bandpass filter 50 is also passed through a rectifier 66 and a logarithmic amplifier 68 which produces a varying dc output voltage which is logarithmically proportional to the amplitude of the rectified signal from rectifier 66.

The signal 63 from converter 62 and the voltage from amplifier 68 are applied to a monostable multivibrator 70 which generates an output pulse train 71 whose pulse repetition rate is determined by the pulse repetition rate of signal 63 and whose pulse width is determined by the voltage from logarithmic amplifier 68. Signal 71 is applied to an RF transmitter 74 for modulating a carrier signal, as illustrated at 75. The modulated carrier is then transmitted by antenna coil 76 or antenna coil 78.

Each of the channels of the transmitter has similar circuitry with the bandpass filters selected to pass the desired frequency band. In each of the channels, the monostable multivibrator generates an output pulse train varying in frequency from about 40 to 400 Hz as this frequency range is particularly suitable for stimulation the cochlea. Thus, each channel generates a similar pulse train varying in frequency from 40 to 400 Hz and with varying pulse width, as described, which are used to modulate carrier signals in the transmitter 74. In the illustrated embodiment employing four channels, the RF transmitter includes four carrier signals with two signals being at 12 MHz and two signals being at 31 MHz. The pulse trains from channel 1 and channel 3 are employed to modulate 12 MHz signals, respectively, and channel 2 and 4 are used to modulate 31 MHz signals, respectively. The carrier signals modulated by signals 1 and 2 are applied to one output coil and the carrier signals modulated by channel 3 and 4 are applied to a second output coil. Because of the frequency difference in the two carrier frequencies applied to each coil, minimum cross-talk results therefrom.

The use of only one transmitter coil per group of receiver coils simplifies fabrication. However, it may be advantageous for other reasons to employ a separate transmitter coil for each of the plural channels involved.

FIG. 3 is an electrical schematic of a multi-channel detector in accordance with an alternate embodiment which includes four independent channels with each channel including a coil 81–84 with coils 81 and 82 magnetically coupled to transmitter coil 76 and the coils 83 and 84 magnetically coupled to the transmitter coil 78. Each of the coils 81–84 is shunted by a capacitor 85 which tunes the coil to 12 megahertz or 31 megahertz, as required for each of channels 1–4. The signal coupled to coil 81 by coil 76 passes through a detector comprising serially connected diode 86 and capacitor 87 and shunt resistor 88. By using pulse modulation and demodulation, a Zener diode can be included in parallel with resistor 88, thus limiting the voltage of the detectors. Accordingly, effects of voltage variations due to changes in alignment of the transmitter and detector coils can be minimized. The detected voltage across output terminals 90 preferably varies from 0 to 3 volts and at a frequency from 40 to 400 Hz, depending on the detected modulation signal.

For tissue stimulation systems with a small number of independent channels simultaneously carrying different signals, especially 2–9 channels, the following method can be used with advantage.

In order to reduce the space required by the plurality of receiver coils, they are arranged in stacked groups. Even though each of the receiver coils is tuned to a different frequency, the mutual coupling of the two and three receiver coils would result in unacceptably high crosstalk, if the coils were merely arranged on top of each other. Arranging the coils in such a way as to compensate their mutual magnetic flux, their mutual inductance vanishes. Thus, two or three independent channels with negligible crosstalk are obtained, using only slightly more space than one channel. Accordingly, coils 81 and 82 are grouped together and spaced from coils 83 and 84, as illustrated in the plan view thereof in FIG. 4. Coils 85′, 86′ and 87′ represent a group of three coils with compensated mutual inductance. Each of the coils has a diameter on the order of 1.5 to 2 centimeters and the spacing between the two groups of coils is approximately 3 centimeters to prevent crosstalk between the groups. As illustrated, coils 81 and 82 and coils 83 and 84 are overlapped to minimize crosstalk between the coils in each group. The overlapping of the coils provides offsetting flux from one coil to the other thereby minimizing distortion or crosstalk between the two coils 81 and 82 are tuned to different frequencies (e.g. 12 MHz and 31 MHz, respectively), each channel of the receiver receives and detects only the signal from the transmission coil to which it is coupled.

Figure 6:
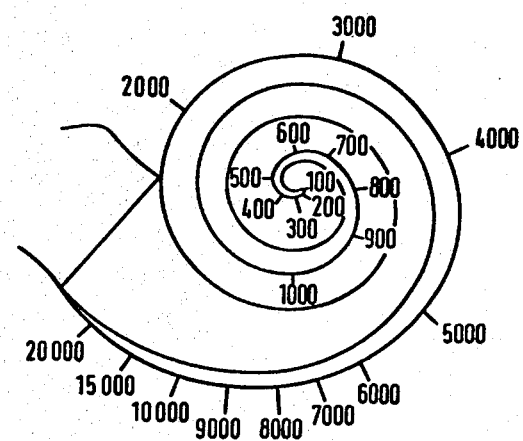
FIG. 6 is a schematic of a cochlea illustrating the frequency response thereof.

The detected signals in each of the receiver channels are connected to a multi-electrode prosthetic device such as the device 90 illustrated in FIG. 5. Each channel can be connected to one or more electrodes having contacts positioned on the prosthetic device to stimulate a region of the cochlea for a desired frequency response. Thus, bipolar stimulation, unipolar stimulation against a remote ground, or a common distributed ground stimulation can be employed. The device comprises an elongated molded body of a silicone elastomer, such as Silastic, in which a plurality of wires, shown generally at 91, are implanted. Each wire is terminated in a ball 92 which is positioned at the surface of the device 90. The spacing of the balls on the surface of the device 90 provides selected frequency response when the device is inserted into the cochlea. As noted in the schematic of a cochlea shown in FIG. 6, the frequency response generated by the cochlea varies from a high frequency at the basal turn of the cochlea and has a progressingly lower frequency response towards the apex of the cochlea. Accordingly, by proper positioning of the electrode contacts or balls 92 within the cochlea, the electrical stimulation of the cochlea provided by the prosthetic device will induce a desired frequency response. By the additional variation of stimulation frequency, a pitch continuum can be achieved.

Figure 7:
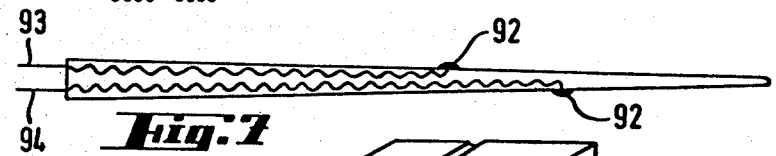
FIG. 7 is a sectioned view of a multi-electrode prosthetic device in accordance with the invention.

FIG. 7 is a section view of the prosthetic device of FIG. 5 illustrating the positioning of wires 93 and 94 within the device. To facilitate illustration only two wires are shown. Each of the wires is wrinkled to provide stress relief and to facilitate flexing of the prosthetic device as it is inserted into the cochlea. In a preferred embodiment the wires are Teflon coated platinum (90%)- iridium (10%) wires having a diameter of 25 microns. The balls at the ends of the wire are 300 microns in diameter and are formed by heating the wires in a flame until the wire tips melt. The balls are arranged in pairs in two diametrically opposed rows. In one embodiment the total diameter of the prosthetic device is 0.9 millimeter and is tapered to about 0.5 millimeter at its tip. Overall length must accommodate an insertion in the cochlea of 20-25 millimeters.

Figure 8:
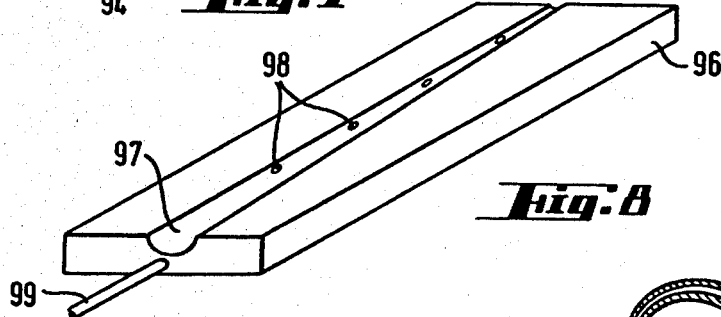
FIG. 8 is a perspective view illustration a mold useful in fabricating the prosthetic device of FIG. 7.

FIG. 8 is a perspective view of the bottom portion 96 of a suitable mold for forming the prosthetic device and includes a centrally disposed tapered channel 97 of the desired device configuration. A plurality of holes 98 are provided in the surface of channel 97 with each of the holes 98 in communication through body 96 with a vacuum line 99. In forming the prosthetic device, the wires are first positioned in the mold cavity with the spherical end portions of the wires placed in holes 98 and maintained in position by means of the vacuum applied to line 99. The mold is then assembled and the cavity defined by channel 97 is filled with Silastic material. The vacuum chuck provided by holes 98 ensures proper positioning of the ball contacts on the surface of the prosthetic device to provide the desired frequency stimulation by the device when inserted into the cochlea.

Figure 9A:
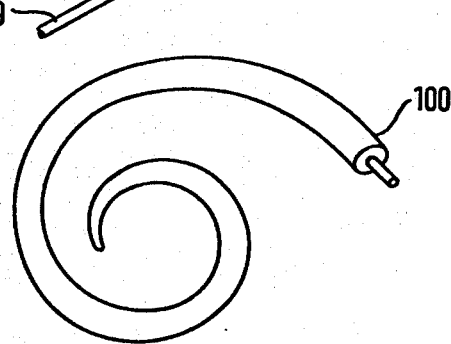
FIG. 9a is an alternative embodiment of a prosthetic device.
Figure 9B:
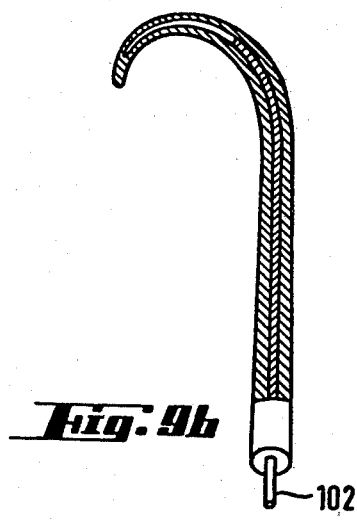
FIG. 9b illustrates the insertion of the device of FIG. 9a into the cochlea.

FIG. 9a is a perspective view of an alternative embodiment 100 of prosthetic device which is molded to conform to the shape of the cochlea. Insertion of the device in the cochlea is illustrated in the section view in FIG. 9b in which a straight stylet 102 such as steel wire is inserted into the molded body 100. The stylet 102 is slowly extracted therefrom as the device is inserted into the cochlea whereby the body 100 reassumes its molded configuration due to the memory properties of the plastic sheath.

It is also envisioned that the external and implanted devices may be configured such that a four or more channel electrode may be disposed within the scala tympani coupled to an implanted receiver, which has a corresponding number of channels, the receiver being driven by an external, single channel sound-processor transmitter. In such an arrangement, either one electrode channel may be chosen for stimulation or a variable number of electrode contacts may be interconnected. In this latter arrangement, different thresholds for different electrode contacts can be taken into account and compensated for by means of electronic circuitry embodied in the dynamic range compression circuits yet to be described.

The arrangement utilizing a four channel implant and an external channel sound-processor has been tested in selected, totally deaf, volunteers who were precluded from using lip reading. In open speech discrimination between 60% and 70% recognition for unknown words or sentences was obtained using stimulation only. This means that the prothesis can already be regarded as a useful aid for the totally deaf.

The embodiment described in conjunction with FIGS. 2 and 3 hereof may be considered to be a pulse circuit implementation in that the sound waveforms are transformed into pulse trains. The possibility exists for implementating the system of the present invention using analogue techniques. That is to say, for both the single channel and the multi-channel external portable stimulators, analogue circuitry may be used for processing the picked-up sound waveforms. In this case, the embodiment illustrated in FIG. 10 may be adopted.

With reference, then, to FIG. 10, there is shown a microphone device 104 for converting impinging sound waves into an electrical signal. This signal is applied to the gain control amplifier 105 and the output thereof is applied to one or more identical channels. As with the embodiment of FIG. 2, in FIG. 10 each of the plural channel(s) is arranged to include the same types of electronic circuits as are shown diagrammatically in channel 1 and, hence, there is no need to replicate these circuits in channels 2, 3 and 4 of FIG. 10.

With reference, then, to channel 1 in FIG. 10, the picked-up and amplified electrical signals from the gain controlled amplifier 105 are applied to a series of band-pass filters 103 (one per signal processing channel), each tuned to pass predetermined frequency bands. Thus, signals falling in the frequency band of 0.25-0.5KHz are relegated to channel 1, while channels 2, 3, and 4 may be arranged to pass signal components having frequencies in the range of 0.5-1.0KHz, 1.0-2.0KHz, and 2.0-4.0KHz, respectively. Following the band-pass filter in each channel is a device referred to as an "isoloudness frequency adjustment" 106. This device insures that irrespective of the frequency band, the signal intensity emanating therefrom will be the same in each channel.

Following the isoloudness frequency adjustment circuit 106 is a dynamic range compression circuit 107. It has been found that when using analogue signal processing techniques, dynamic range compression as well as the aforementioned isoloudness frequency adjustment are very important features of the external sound processor because the dynamic range between stimulus intensities necessary to cause threshold sensations and excessively loud sensations is significantly smaller in the case of hearing induced by electrical stimulation than for normal hearing. In some cases there also seems to be a relationship between the stimulation frequency and the threshold intensities. The dynamic range compression circuit uses non-linear elements which are preferably logarithmic in nature. However, alternate non-linear characteristics, such as those obeying a power law, may be implemented with a Type LH0096 integrated function circuit device available through National Semiconductor Co. A piece-wise linear function, or some other suitable shape may also prove expedient. As will be explained in greater detail hereinbelow, the function may be implemented by suitably connected differential amplifiers or operational amplifiers using diode networks or diode connected transistors.

In order to reduce the introduction of unwanted frequencies by this dynamic range compression, the non-linear device used may be driven by a frequency shifted signal. The even order harmonic distortion products may then be eliminated by a narrow band rf-band pass filter before the signal is down-mixed to the audio range. Still another possibility for reducing distortion products is to employ non-linearities within octave wide bands.

It is also envisioned that a gain controlled amplifier be employed which possesses sufficiently small attack and release time constants of 2 to 10 ms and 100 to 200 ms respectively, the desired shaping of the gain characteristics of the amplifier being achieved through the insertion of proper non-linear devices into its control signal path.

While in FIG. 10 the dynamic range compression circuit 107 is shown as following the isoloudness frequency adjustment circuit, those skilled in the art will realize that the dynamic range compression circuit may just as well preceed the isoloudness frequency adjustment circuit 106 in whch case only very slight, but accurate frequency shaping is necessary.

With continued reference to FIG. 10, a multi-channel stimulator is seen as consisting of several, essentially identical signal processing channels with separate rf-transmission circuits. Each channel represents a particular frequency band. These bands are selected by the band pass filters 103. In the case of a single channel stimulator, only one of these channels is used. The band pass filter 103 may then be deleted in the single channel arrangement.

The dynamic range of the acoustic signal picked by the microphone amounts to more than 80 dB. This large dynamic range has to be transformed into the range of stimulation intensities of approximately 10–20dB. This is achieved by dynamic range compression circuitry 107 and/or an input dependent gain controlled amplifier, such as 105 in FIG. 10. One advantage the use of the gain controlled amplifier has over dynamic range compressions using non-linear elements is the small amount of additional non-linear distortion introduced. Offsetting this advantage may be the fact that for a sudden onset of a very loud signal, annoying peaks may appear at the output. Therefore, dynamic range compression and gain control are recommended for simultaneous use.

The circuit 106 which is used for the adjustment of frequency response to the patient's frequency dependence of isoloudness characteristics, contains frequency dependent components such as resistance-capacitance (RC) or inductance-capacitance (LC) combinations.

The amplitude modulated transmitter 108 with its tuned tank circuit 109 is used to transmit the processed signal to the implanted tuned antenna 110 of the receiving circuit and to the demodulator 111. The demodulated signal is then coupled to appropriate electrode pairs in the implanted multi-electrode prosthetic device disposed in the cochlea.

Figure 11:
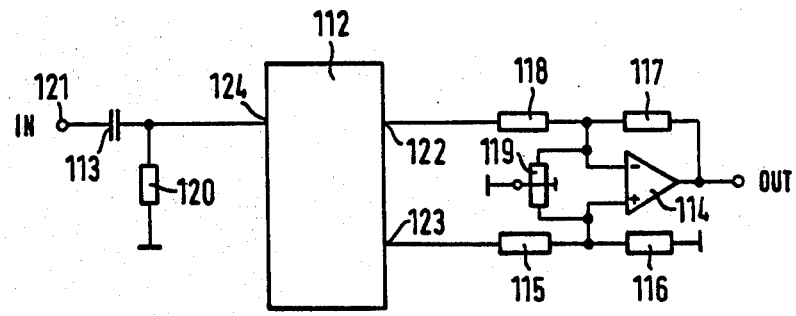
FIG. 11 is an electrical schematic circuit diagram of one arrangement for performing dynamic range compression.

Referring next to FIG. 11, there is shown the details of one way of implementing of the dynamic range compression circuit represented by block 107 in FIG. 10. The dynamic range compression circuit includes an integrated circuit 112 which may, for example, be a Texas Instruments Type 441 device and as such, contains four differential amplifiers whose outputs are paralleled and whose inputs are driven via voltage dividers of varying attenuation. The differential voltage between the output terminals 122 and 123 depends logarithmically on the input voltage at terminal 124. The input voltage applied to terminal 121 is coupled to the intergrated circuit's input 124 by means of a coupling capacitor 113 which serves to prevent any dc voltage from reaching the input. The resistor 120 is used to establish dc ground potential at the input of the IC differential amplifier device. The differential voltage developed between the output terminals 122 and 123 is transformed to single ended output in a conventional manner. That is, an operational amplifier 114 together with resistors 115, 116, 117 and 118, causes the amplifier 114 to function as a differential amplifier. The potentiometer 119 which is coupled between the inverting and non-inverting inputs of the differential amplifier 114 may be used to adjust the circuit's off-set voltage.

Figure 12:
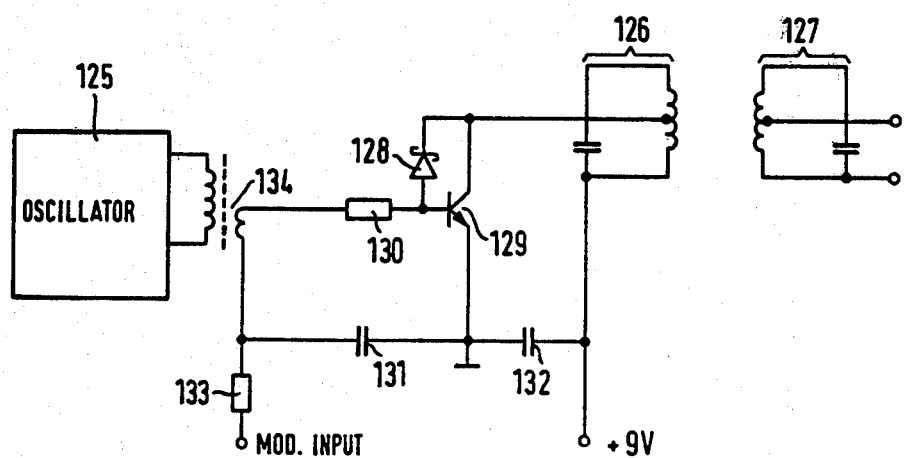
FIG. 12 is a schematic diagram of a preferred arrangement for the AM transmitter used in the embodiment of FIG. 10.

The details of an amplitude modulated transmitter for use as transmitter 108 in FIG. 10 are set forth in greater particularity in FIG. 12. It includes an rf oscillator 125 which functions to generate the carrier frequency and a power amplifier stage driven thereby. The carrier frequency may typically be 12MHz, but limitation to this value is not intended. The output of the power amplifier stage drives a tuned tank circuit 126 which is inductively coupled to the implanted receiver circuit 127. The combination of the inductively coupled tuned circuits form a band-pass filter. The transmitter coil is positioned relative to the receiver coil by monitoring the voltage across the transmitter coil while varying the position of the two. When the observed voltage is reduced to approximately one-half of its maximum value, optimum positioning is found to exist.

With continued reference to FIG. 12, the audio signal used to modulate the carrier is coupled to the base of the transistor 129 by way of resistor 133, transformer secondary winding 134, and the resistor 130. The resistor 130 is selected to obtain adequate rf output power without having to change the number of turns of the coupling coil 134 which, of course, is a more difficult procedure. The capacitors 131 and 132 provide an rf bypass at the modulation signal input and at the power supply, respectively. A Schottky diode 128 connected between the base and the collector of the power transistor 129 functions to prevent unwanted parasitic oscillations in the event of inadvertant saturation thereof.

The tank circuit 126 of the transmitter is mounted to an ear-hook made of acrylic glass which is used to position the circuit directly over the implanted receiver circuit. The transmitter is minaturized so that it also may be disposed on this ear-hook. As such, any rf radiation from the device is minimized in that the rf carrying elements are shorter than 2 cm.

Figures 13, 13A, 13B:
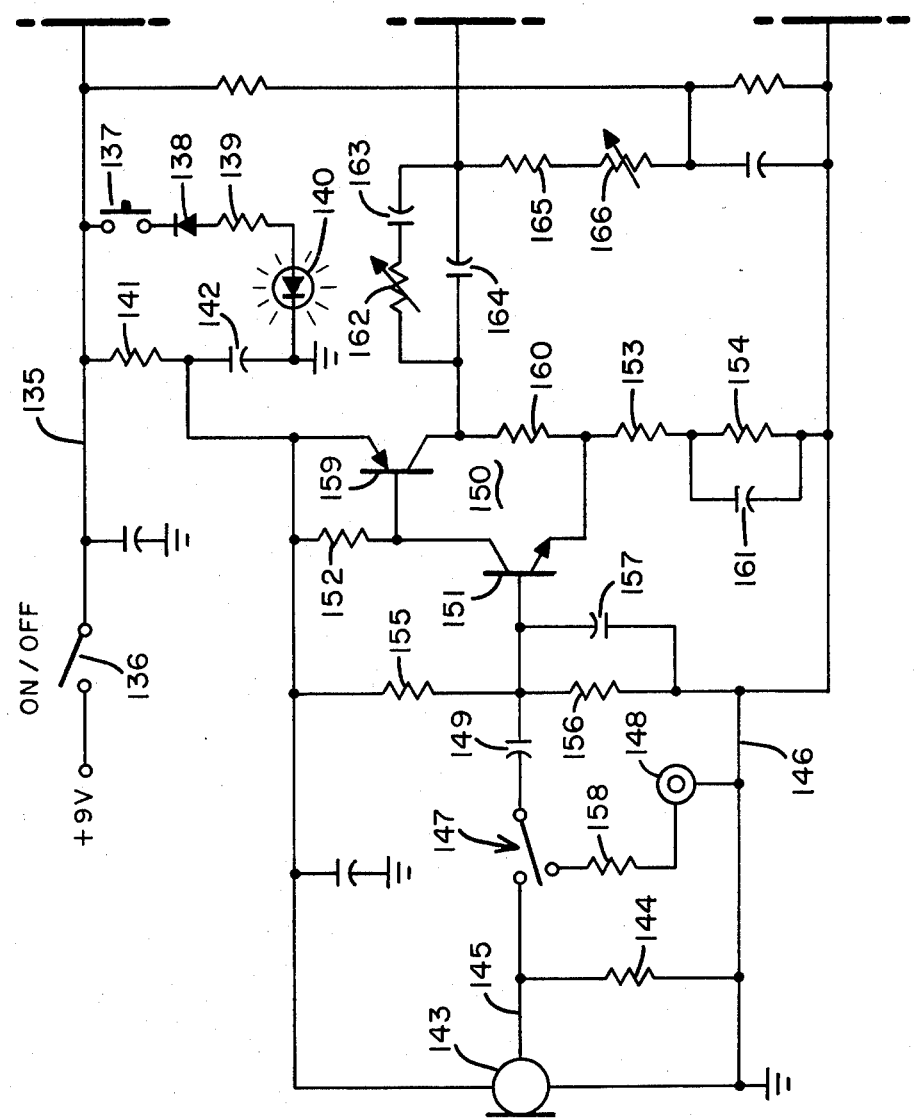
FIGS. 13a and 13b, when arranged as shown in FIG. 13, show a schematic electrical diagram of an alternative analogue speech processing channel which may be used in implementing the system of FIG. 10.
Figure 13B:
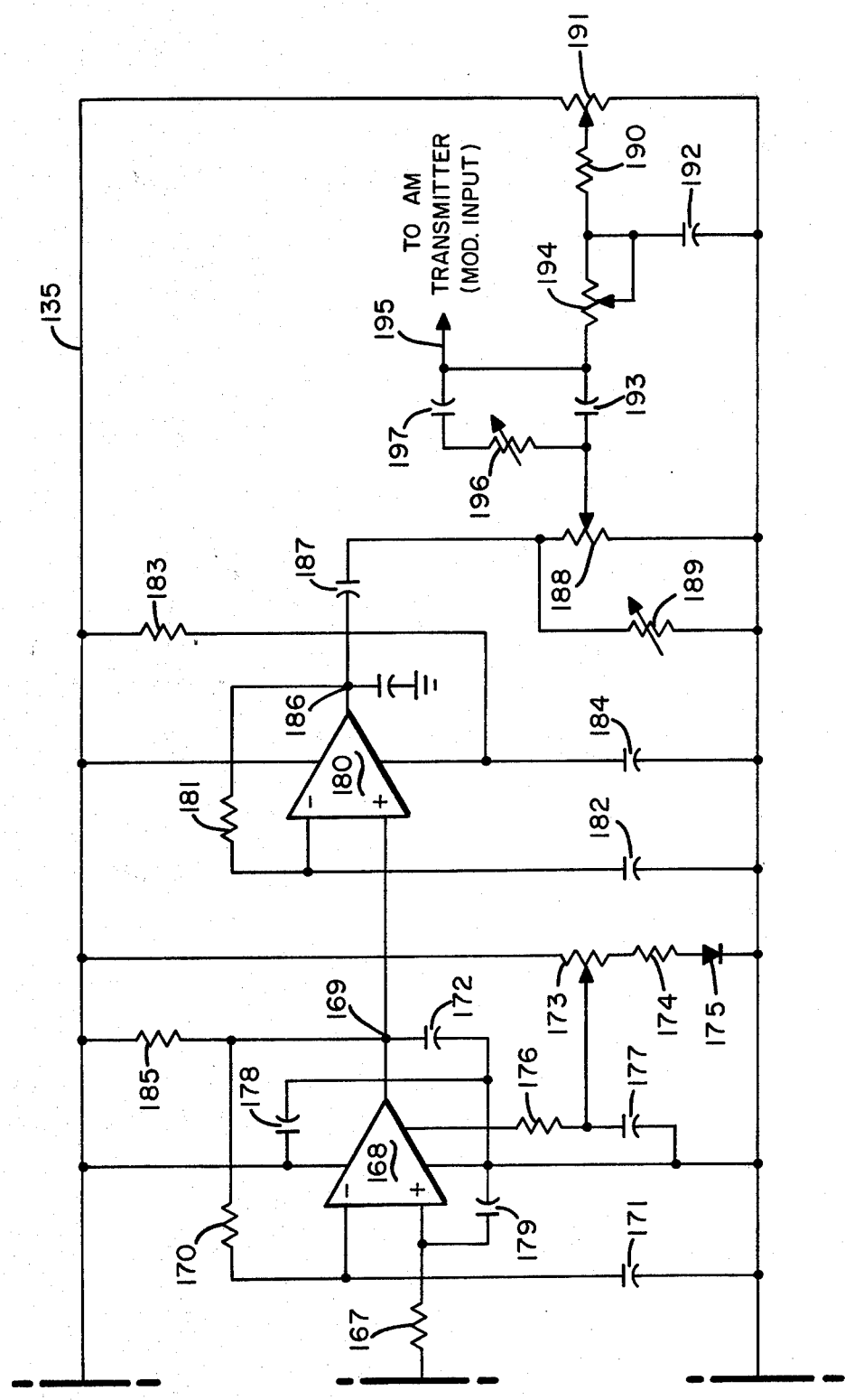

Referring next to FIGS. 13a and 13b, there is shown an electrical schematic diagram of an arrangement which may be used in implementing the gain controlled amplifier 105, the isoloudness frequency adjustment 106 and the dynamic range compression circuit 107 in the analogue, single or multi-channel speech processor transmitter. Number 135 refers to the B+bus which is arranged to be connected through an on/off switch 136 to a source of positive potential, typically a nine volt nickel cadmium rechargable cell. Connected between the positive bus 135 and ground is a series circuit including a push buttom switch 137, a zener diode 138, a resistor 139 and a light emitting diode 140. Closure of the push-button switch will cause the LED 140 to glow if the battery potential is above a pre-determined threshold value. A zener diode 138 establishes this threshold value. The resistor 141 and capacitor 142 which connect between the positive bus 135 and ground serve to decouple the power supply from the microphone and the pre-amplifier stage yet to be described.

Identified by numeral 143 is a sensitive, miniature microphone containing a field effect transistor (not shown) which produces a current output which varies in response to the undulations of received sound waves. A resistor 144 is coupled between the signal output lead 145 of the microphone and a ground bus 146. The microphone output lead is coupled to a first terminal of a single-pole, double-throw switch 147 which may be used to alternatively select the microphone output or the output from a external jack 148. This jack provides a means whereby an external microphone, telephone adapter, cassette recorder, T.V. set, etc. may provide the input to the speech processing unit.

A capacitor 149 is used to ac couple the microphone output or the signal coming from the jack 148 to the input of a low noise preamplifier identified generally by numeral 150. Specifically, a first NPN transistor 151 has its base electrode coupled through the capacitor 149 to the signal source and its collector electrode coupled through a load resistor 152 to an intermediate voltage bus 153, this latter bus being coupled to the B+ bus 135 by way of the resistor 141. The emitter electrode of the transistor 151 is coupled through resistors 153(a) and 154 to the ground bus 146. Bias for the transistor 151 is provided by a voltage divider which includes resistors 155 and 156 connected in series between the intermediate bus 153 and the ground bus 146. The capacitor 157 along with the resistor 158 provide isolation and prevent rf interference from any external source from adversely affecting circuit operation.

The collector electrode of the transistor 151 is also connected to the base or control electrode of a PNP transistor 159. The emitter electrode of this latter transistor is connected to the intermediate bus 153 and its collector is coupled by a resistor 160 to the junction between the emitter electrode of transistor 151 and the resistor 153(a). It can be seen, then, that the collector current for transistor 151 is determined by the resistor 152 while the collector current of the transistor 159 is determined by a voltage divider including resistors 155 and 156 as well as the resistor 153(a) and 154. The capacitor 161 is included to prevent the resistor 154 from reducing the voltage gain of the pre-amplifiers stage.

The function performed by the isoloudness frequency adjustment 106 in FIG. 10 is somewhat distributed in the circuit arrangement of FIGS. 13a and 13b. Specifically, the coupling capacitor 149 and the resistor 156 form a hi-pass filter as does the combination of the resistor 162, capacitor 163, the capacitor 164, the fixed resistor 165 and the variable resistor 166. Analysis of this circuit combination reveals that the hi-pass filter possesses two poles and one zero. The first pole of the hi-pass filter is determined by the component values of the capacitor 164 and the resistors 165 and 166. The zero characteristic of the hi-pass filter is determined by the component values of the resistor 160 and the capacitor 164 while the second pole of the filter is determined by the value of capacitor 163 and the resistors 165 and 166.

The output from the hi-pass filter stage is coupled through a resistor 167 to the non-inverting input of an operational transconductance amplifier (OTA) 168 which is configured to function as a low pass filter. Specifically, connected between the output terminal 169 of the OTA 168 and its inverting input is a feedback resistor 170. A capacitor 171 connected between the inverting input and the ground bus 146 serves to decouple the inverting input from the ac signal at the amplifier output. A further capacitor 172 is connected between the output terminal 169 of the OTA 168 and the ground bus. This capacitor along with the resistor 170 provides the low-pass filter characteristics to the OTA stage 168. Connected between the positive bus 135 and the negative bus 146 is a series combination of a potentiometer 173, and fixed resistor 174 and a semiconductor diode 175. The wiper arm of the potentiometer 173 is coupled to the bias network of the OTA device 168 which includes the resistor 176 and decoupling capacitor 177. By virtue of this connection, the gain of the amplifier 168 may be adjusted and the sensitivity of the sound processor thereby controlled.

The capacitor 178 across the power supply bus is selected so as to prevent unwanted oscillation while the resistor 167 and a further capacitor 179 are effective to prevent radio frequency interference from deleteriously effecting system performance.

The component values for the voltage divider including the potentiometer 173, the fixed resistor 174 the semi-conductor diode 175 and the resistor 176 permit manual gain control in the range of −20 db to 40 db, which, in turn, determines the systems sensitivity.

The output from the variable gain amplifier/filter stage appearing at junction 169 is directly coupled to the non-inverting input of a further operational transconductance amplifier 180. The inverting input of the OTA 180 is coupled to the common junction between a feedback resistor 181 and a capacitor 182, these two latter components providing the appropriate biasing for the OTA. A resistor 183 coupled between the positive bus 135 and the amplifier bias current (ABC) input of the OTA 180 is selected to provide a desired output current level. The capacitor 184, then, decouples that dc level from the power supply. Bias current for the stage 180 is also provided via resistor 185 which is connected between the positive bus 135 and the non-inverting input terminal of the OTA 180.

Connected between the output terminal 186 of the non-linear amplifier stage 180 and the ground bus 146 is a series combination of a filter capacitor 187 and a potentiometer 188. A variable resistor 189 is connected directly and parallel with the potentiometer 188. The capacitor 187 serves to block any dc voltage appearing at the output of the non-linear amplifier 180 from reaching the potentiometer 188. The output voltage appearing on the wiper arm of the potentiometer 188 is the signal which is used to modulate the amplitude modulated transmitter 108 in FIG. 10. As has been mentioned earlier, the transmitter employs either a 12 or a 31 MHz carrier and the base line for the modulation envelope is controllable by adjusting the variable resistor 189 and the potentiometer 188. Actually, the variable resistor 189 sets the maximum output voltage which is usable by the patient. It prevents inadvertent over-stimulation. The fixed resistor 190 and the potentiometer 191 allow adjustment of the carrier level of the AM transmitter so that undue distortion can be prevented. The capacitor 192 again is included for the purpose of decoupling the ac signals from the dc supply.

The capacitor 193 and the potentiometer 194 together with resistor 196 and capacitor 197 comprises a hi-pass filter contributing also to the isoloudness frequency adjustment 106 in FIG. 10. The function of the components 193, 194, 196 and 197 is equivalent to that of the components 164, 165 plus 166, 162 and 163, respectively. Depending upon the individual patient's needs, either of these two filter arrangements may be used individually or both may be included.

From the foregoing description of the schematic of FIGS. 13a and 13b, then, it can be seen that the circuit is effective to perform the isoloudness control function as well as the dynamic range compression and variable control features reflected in the block diagram of FIG. 10.

Figure 14:
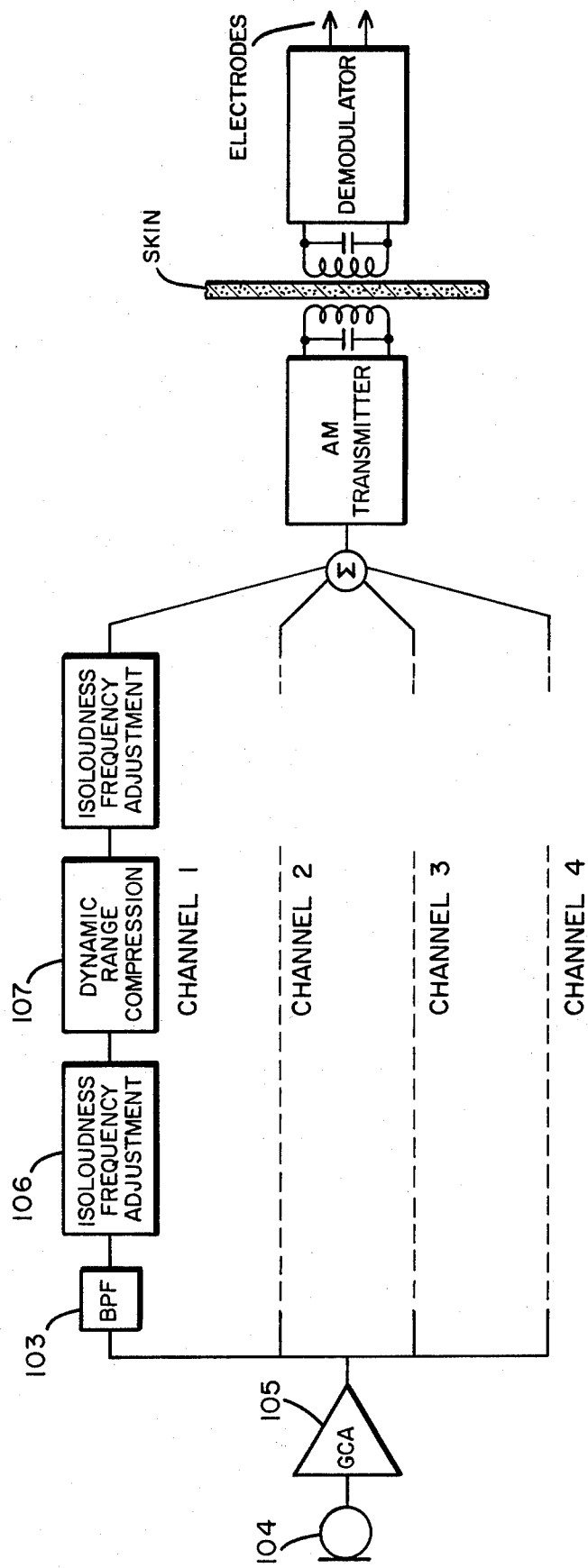
FIG. 14 is a block diagram of a single channel speech processing system for use in the stimulation of auditory nerves.

The embodiment of an analogue transmitter configuration shown in FIG. 10 contemplates the use of plural AM transmitters, one for each signal processing channel. In FIG. 14 there is shown a further implementation wherein the outputs from the plural signal processing channels are joined at a summing node and only a single AM transmitter module is utilized. The AM transmitter drives a tuned circuit which is inductively coupled through a tissue barrier to an implanted single channel receiver, the receiver typically being a diode detector demodulator circuit of conventional design. A single channel electrode which may be fabricated in accordance with the teachings of this specification and involving only a single ball-type stimulating contact along with an indifferent electrode is driven by the demodulator circuit.

It is also contemplated that the embodiment shown in FIG. 10 can be simplified by employing a single speech processing channel, such as channel 1 in FIG. 14, feeding the AM transmitter module.

Figure 15:
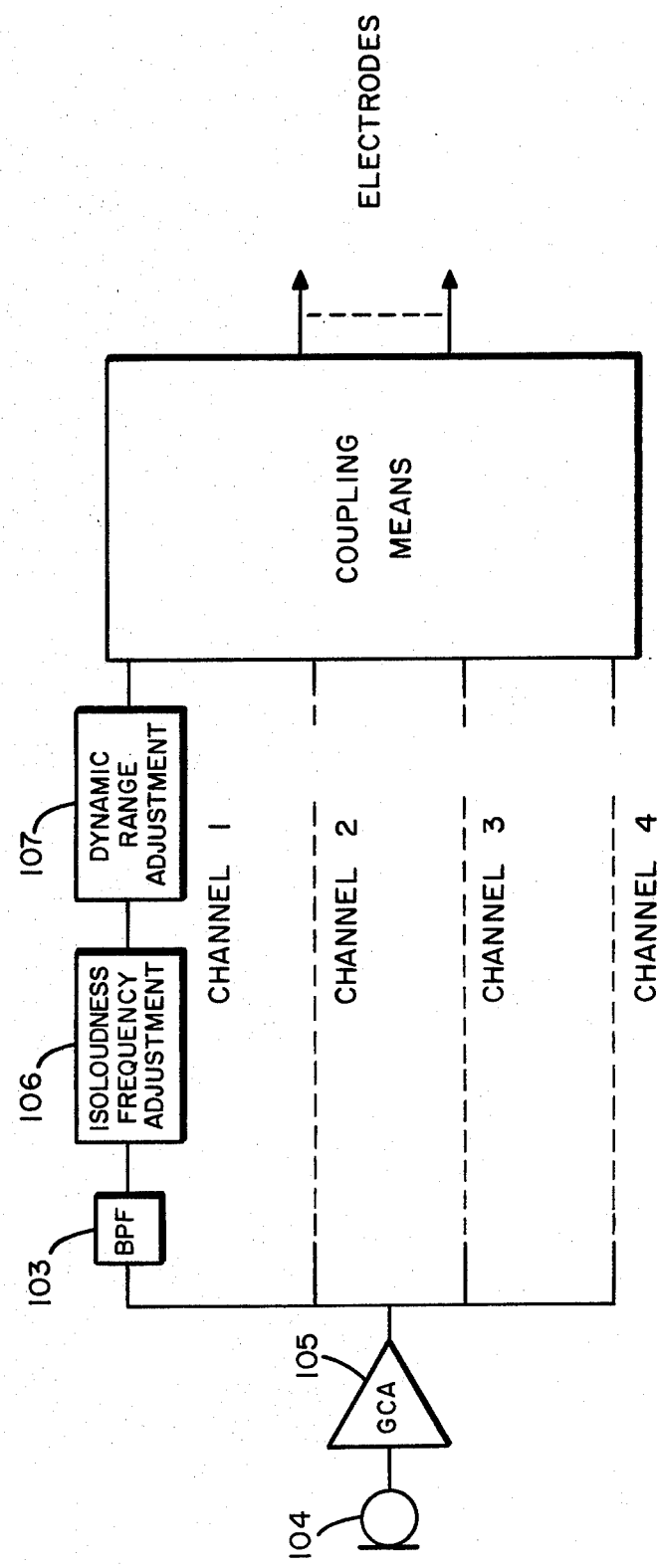
FIG. 15 is a block diagram illustrating an alternative means of coupling an external signal processing device to an implanted prosthesis.

FIG. 15 is a block diagram representation of a speech processing system in which one or more signal processor channels, each including a band-pass filter 103, an isoloudness frequency adjustment 106 and a dynamic range adjustment 107 may be coupled in a manner other than via a radio transmission link to the implanted electrodes. Typically, the coupling means shown in FIG. 15 may be a percutaneous insulated lead having wires providing a conductive link between one or more signal processing channels and the electrodes of the prosthetic device.

The method of auditory stimulation utilizing the multi-frequency system in accordance with the present invention provides improved hearing in the deaf and hard of hearing. The use of frequency band signals enhances the perceived sound and the selective stimulation of the cochlea enhances the auditory response. Since the receiver comprises passive devices, no power supply other than the transmitted signals is required. The prosthetic device is readily manufactured with exact electrode positioning to achieve desired frequency response when stimulating the cochlea. While pulse modulation is employed in the preferred embodiment, other modulations such as amplitude or frequency can be employed. Analogue signals can be employed as well as pulsed or digital signals in practicing the invention. While in the described embodiment the audio frequency bands are transformed to corresponding signals having frequencies of 40-400 Hz, the corresponding signals can have the same frequencies as the audio bands or the frequencies may be unrelated.

Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

We claim:

1. A multi-frequency system for electrical stimulation of selected tissue groups comprising:
   (a) transmission means for transmitting a plurality of carrier signals each of which is modulated by a signal representing a band of frequencies, said transmission means including a plurality of signal processing channels corresponding to the plurality of bands of frequencies in the audio range, each signal processing channel including a band-pass filter for selecting a band of audio frequency signals, means for compressing the dynamic ranges of said audio frequency signals, means for compensating the loudness of said audio frequency signals dependent upon their frequency; and a transmitter for modulating a carrier signal with the processed audio frequency signal;
   (b) multi-channel receiver means for receiving said transmitted signals with each receiving channel responsive to one of said transmitted signals;
   (c) electrode means for electrically contacting said selected tissue groups; and
   (d) means connecting a signal from each of said receiving channels to said electrode means whereby said electrode means provides electrical stimulation.

2. A multi-frequency system as in claim 1 wherein said multi-channel receiver means includes four channels, each channel including a receiving coil, said transmitter means including two transmitting coils with each of said transmitting coils transmitting two modulated carrier signals, a first two of said receiving coils being inductively coupled to one of said transmitting coils, the other two of said receiving coils being inductively coupled to the other of said transmitting coils.

3. A multi-frequency system as in claim 1 wherein said multi-channel receiver means includes four channels, each channel including four receiving coils, said transmitting means including four transmitting coils with each of said transmitting coils transmitting a modulated carrier signal to a corresponding receiving coil, and with each of said transmitting coils being inductively coupled to a corresponding receiving coil.

4. A multi-frequency system as in claim 1 wherein said means for compression of dynamic range comprises a non-linear element.

5. A multi-frequency system as in claim 4 wherein said non-linear element is a function circuit implementing a power law associated with each of said plurality of channels.

6. A multi-frequency system as in claim 4 wherein said non-linear element is a logarithmic amplifier associated with each of said plurality of channels.

7. The multi-frequency system as in claim 1 wherein said means for compression of dynamic range comprises a gain controlled amplifier disposed in said signal processing channels.

8. For use in a system for transcutaneous electrical stimulation of a selected tissue group, a signal processing device comprising: p1 (a) at least one signal processing channel including:
   1. band-pass filtering means for passing a discrete band of frequencies through said signal processing channel, 2. means for modifying the amplitude of the filtered signals as a function of the frequency band, and
3. means for compressing the dynamic range of the filtered signals to a predetermined range;

(b) means for coupling the signals to said selected tissue group.

9. The signal processing device as in claim 8 wherein said means for coupling said signals to said selected tissue group comprises a percutaneous lead having a plurality of wires joining said signal processing channel(s) to said selected tissue group.

10. The signal processing device as in claim 8 wherein said means for coupling comprises radio frequency transmitter means coupled to said signal processing channel whereby an R.F. carrier wave is modulated by the signals emanating from said signal processing channel.

11. The signal processing device as in claim 8 and further including an input device for providing a time-varying electrical signal to said signal processing channel and a gain controlled amplifier connected between said input device and said signal processing channel.

12. The signal processing device as in claim 8 wherein said means for modifying the amplitude of said filtered signals comprises an operational transconductance amplifier means coupled to receive the output from said band-pass filtering means for producing an output current proportional to the voltage signal from said band-pass filtering means; and means for adjusting the gain of said operational transconductance amplifier whereby the sensitivity of said signal processing channel can be established.

13. A multi-frequency system for electrical stimulation of selected tissue group comprising:

(a) at least one signal processing channel including:

1. band-pass filtering means for passing a discrete band of frequencies through said signal processing channel,
2. means for modifying the amplitude of the filtered signals as a function of the frequency band, and
p2 3. means for compressing the dynamic range of the filtered signals to a predetermined range;

(b) radio-frequency transmitter means coupled to said signal processing channel for modulating an RF carrier wave by the signals emanating from said signal processing channel;

(c) a radio-frequency signal receiver adapted to be implanted subcutaneously, said receiver being coupled to the output of said radio-frequency transmitter means;

(d) electrode means for establishing electrical contact with said selected tissue group; and (e) means connecting said receiver to said electrode means.

14. A multi-frequency system as in claim 13 wherein said transmitter means and said receiver include a plurality of transmitting and receiving channels, respectively.

15. The multi-frequency system as in claim 13, wherein said transmitter means includes an antenna coil for radiating the modulated RF carrier wave.

16. The multi-frequency system as in claim 15, and further including an ear-hook member, adapted to be removably secured to a wearer's auricle and means physically attaching said radio frequency transmitter means and said antenna coil to said ear hook member.

17. The multi-frequency system as in claim 15, wherein said radio-frequency signal receiver is implanted subcutaneously behind the patient's auricle and includes a receiving coil in general alignment with said antenna coil when said ear-hook is secured to said wearer's auricle.

* * * * *

UNITED STATES PATENT AND TRADEMARK OFFICE
CERTIFICATE OF CORRECTION

PATENT NO. : 4,357,497

DATED : November 2, 1982

INVENTOR(S) : Ingeborg J. Hochmair et al

It is certified that error appears in the above-identified patent and that said Letters Patent are hereby corrected as shown below:

Column 14, Line 64, "p1" should be deleted.

Column 16, Line 6, "p2" should be deleted.

*Signed and Sealed this*

*Twenty-fifth* Day of *January 1983*

[SEAL]

Attest:

GERALD J. MOSSINGHOFF

*Attesting Officer*   *Commissioner of Patents and Trademarks*